United States Patent
Yoshida

(10) Patent No.: US 9,972,079 B2
(45) Date of Patent: May 15, 2018

(54) WAFER APPEARANCE INSPECTION APPARATUS

(71) Applicant: Hitachi High-Technologies Corporation, Minato-ku, Tokyo (JP)

(72) Inventor: Mitsuhiro Yoshida, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 234 days.

(21) Appl. No.: 14/889,986

(22) PCT Filed: Apr. 28, 2014

(86) PCT No.: PCT/JP2014/061892
§ 371 (c)(1),
(2) Date: Nov. 9, 2015

(87) PCT Pub. No.: WO2014/208193
PCT Pub. Date: Dec. 31, 2014

(65) Prior Publication Data
US 2016/0125590 A1 May 5, 2016

(30) Foreign Application Priority Data
Jun. 24, 2013 (JP) ................. 2013-131486

(51) Int. Cl.
*H04N 7/18* (2006.01)
*H04N 9/47* (2006.01)
(Continued)

(52) U.S. Cl.
CPC ....... *G06T 7/0004* (2013.01); *G01N 21/8851* (2013.01); *G01N 21/9501* (2013.01);
(Continued)

(58) Field of Classification Search
CPC ................ G06T 7/0004; G01N 21/8851
See application file for complete search history.

(56) References Cited

U.S. PATENT DOCUMENTS 7,925,072 B2 * 4/2011 Chen .................. G06T 7/001
356/388
2002/0113234 A1 8/2002 Okuda et al.
(Continued)

FOREIGN PATENT DOCUMENTS

JP 2000-124281 A 4/2000
JP 2002-323458 A 11/2002
(Continued)

OTHER PUBLICATIONS

International Preliminary Report on Patentability (PCT/IB/338 & PCT/IB/373) issued in PCT Application No. PCT/JP2014/061892 dated Jan. 7, 2016 including English translation of document C2 (Japanese-language Written Opinion (PCT/ISA/237)) previously filed on Nov. 9, 2015 (Ten (10) pages).
(Continued)

*Primary Examiner* — Hung Dang
*Assistant Examiner* — Girumsew Wendmagegn
(74) *Attorney, Agent, or Firm* — Crowell & Moring LLP

(57) ABSTRACT

Provided is a wafer appearance inspection apparatus that can segmentize an inspection target region, enable expedited execution of an operation to set a sensitivity threshold to each region, and enhance the inspection efficiency. Pattern matching between the image region of a part of a standard wafer, which is defined as a template region, and the entire image region of the standard wafer is performed to compute an image editing value. The computed image editing value is used to edit an inspection target image. A region for which a threshold is to be set can be automatically confirmed by roughly specifying the region from among edited image regions displayed on the display. The confirmed region and a similar pattern region are searched and displayed. When the similar region is selected, the initial sensitivity threshold is displayed, and a change is made on an as-needed basis.
(Continued)

The region of the set sensitivity threshold is displayed by the display color corresponding to the determined threshold. Inspection is executed according to the set threshold.

4 Claims, 17 Drawing Sheets

(51) Int. Cl.
*G06T 7/00* (2017.01)
*G01N 21/956* (2006.01)
*G01N 21/95* (2006.01)
*H01L 21/66* (2006.01)
*G01N 21/88* (2006.01)
*G06K 9/62* (2006.01)

(52) U.S. Cl.
CPC ......... *G01N 21/956* (2013.01); *G06K 9/6202* (2013.01); *G06T 7/001* (2013.01); *H01L 22/12* (2013.01); *G01N 2021/8887* (2013.01); *G06K 2009/6213* (2013.01); *G06T 2207/20021* (2013.01); *G06T 2207/30148* (2013.01)

(56) References Cited

U.S. PATENT DOCUMENTS

| | | |
|---|---|---|
| 2005/0174457 A1 | 8/2005 | Yoshino et al. |
| 2008/0219545 A1 | 9/2008 | Chen et al. |
| 2015/0170355 A1 | 6/2015 | Yoshida |

FOREIGN PATENT DOCUMENTS

| | | |
|---|---|---|
| JP | 2004-226908 A | 8/2004 |
| JP | 2005-223765 A | 8/2005 |
| JP | 2010-522316 A | 7/2010 |
| JP | 2010-283088 A | 12/2010 |
| JP | 2012-49503 A | 3/2012 |
| JP | 2014-22662 A | 2/2014 |

OTHER PUBLICATIONS

International Search Report (PCT/ISA/210) issued in PCT Application No. PCT/JP2014/061892 dated Jul. 15, 2014 with English-language translation (five (5) pages).

Japanese-language Written Opinion (PCT/ISA/237) issued in PCT Application No. PCT/JP2014/061892 dated Jul. 15, 2014 (five (5) pages).

* cited by examiner

Fig. 6A
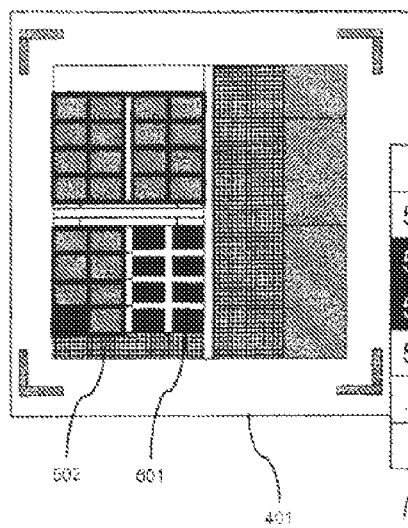
Fig. 6B
| | X | Y |
|---|---|---|
| 503 | 30 | 20 |
| 504 | 40 | 20 |
| 505 | 50 | 20 |
| 506 | 30 | 50 |
| ... | ... | ... |
Fig. 6C
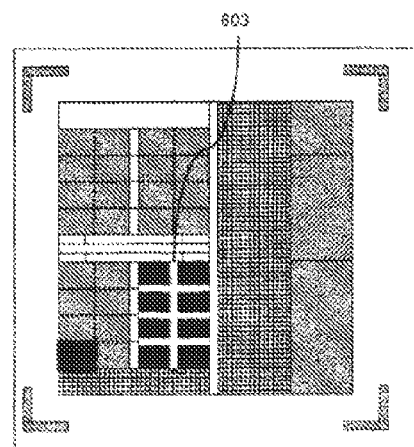
Fig. 7A
AREA SEARCH
(EFFECTIVE FOR CELL AREA)
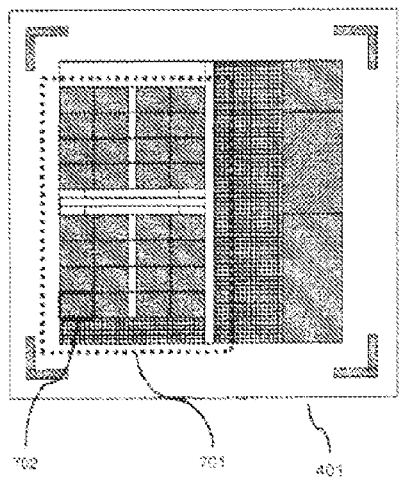
Fig. 7B
LINE SEARCH
(EFFECTIVE FOR LOGICAL PORTION)
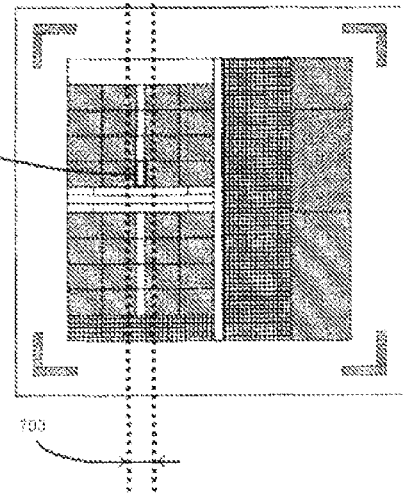

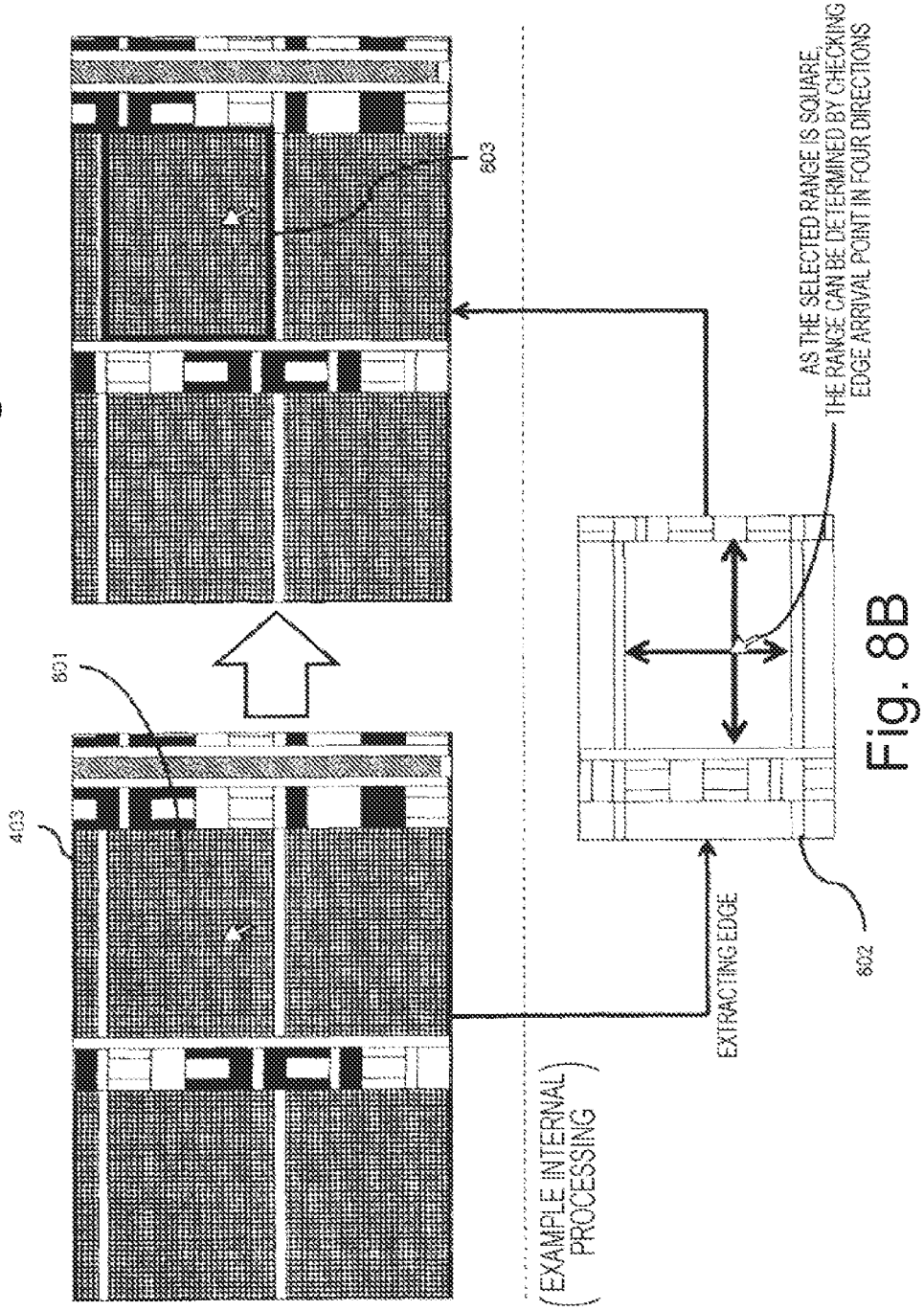

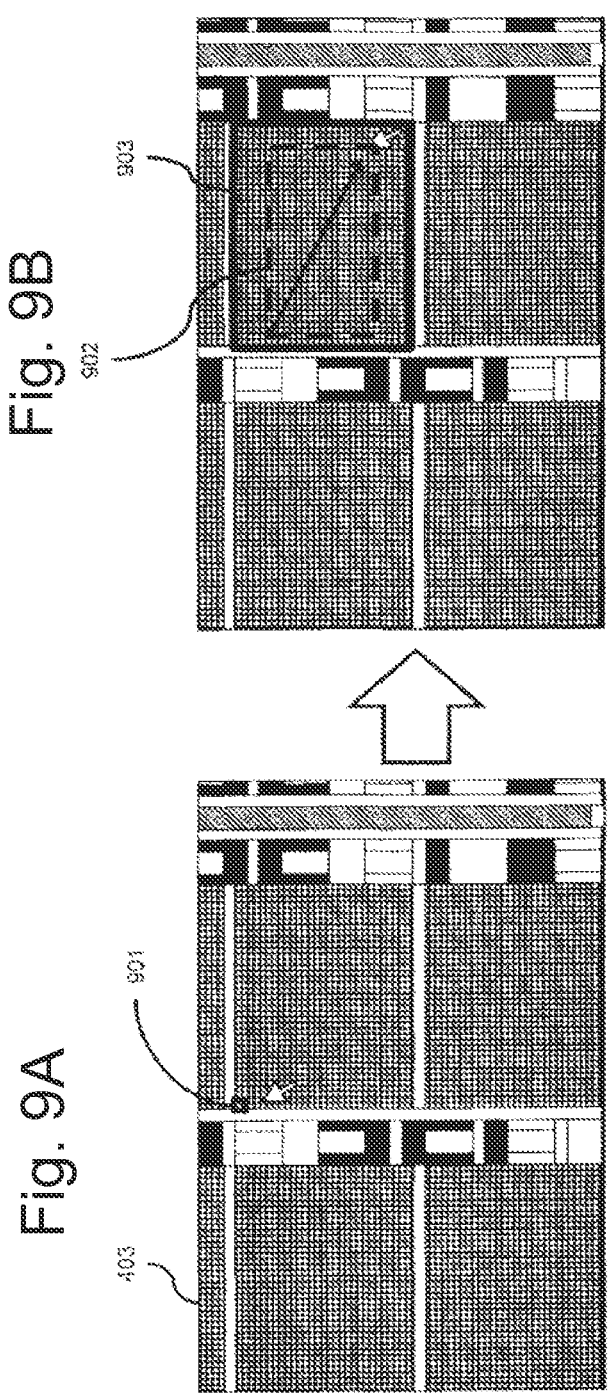

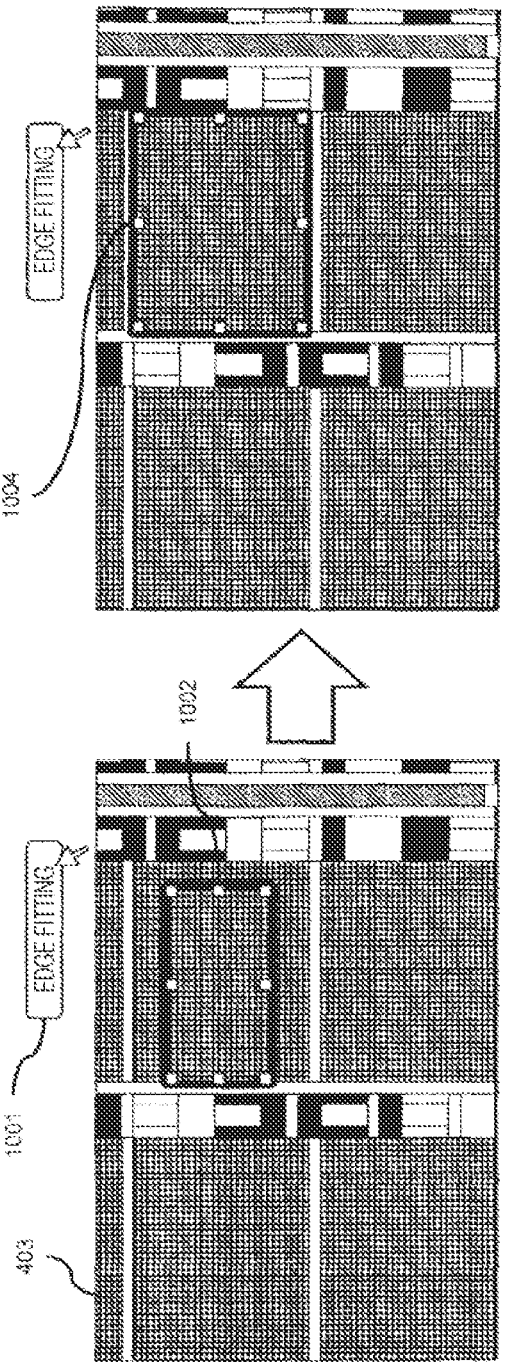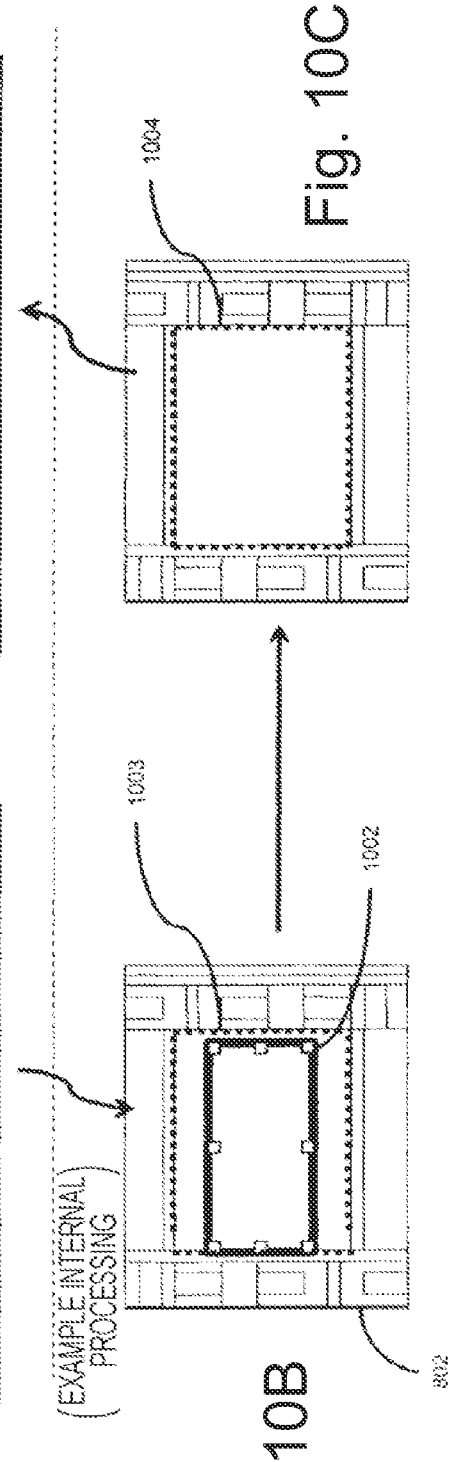

Fig. 11A
Fig. 11B
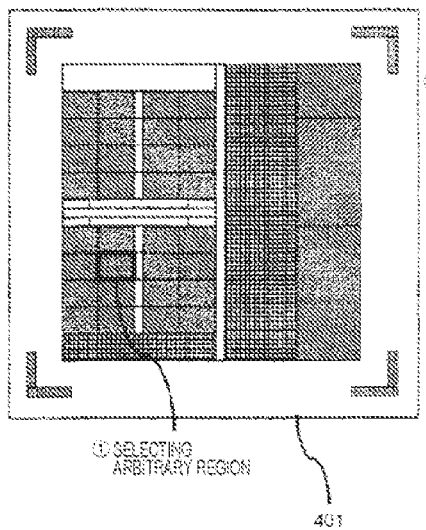
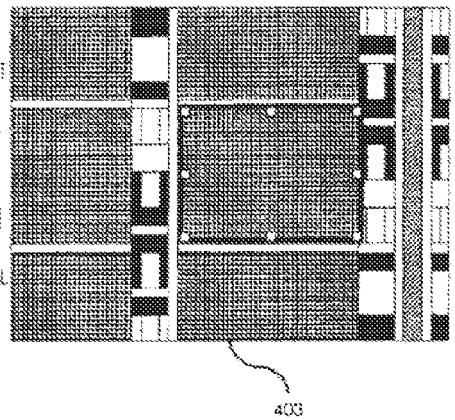
FIG. 12
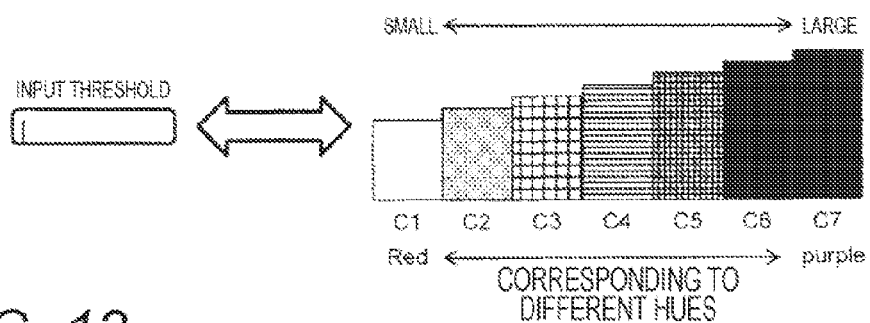
FIG. 13
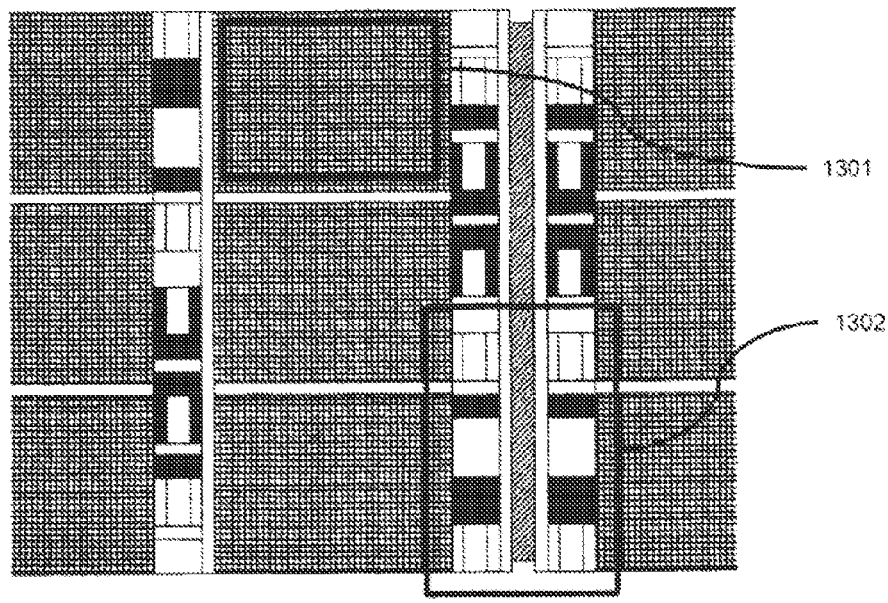

WAFER APPEARANCE INSPECTION APPARATUS

TECHNICAL FIELD

The present invention relates to a wafer appearance inspection apparatus that inspects a surface defect of a wafer during a semiconductor device manufacturing process.

BACKGROUND ART

In a semiconductor device manufacturing process, a wafer appearance inspection apparatus is used. A recipe needs to be prepared to automatically perform inspection using a wafer appearance inspection apparatus. However, a part of recipe preparation inevitably requires human assistance.

Operations requiring human assistance include an operation to change the detected sensitivity threshold setting depending on the location of a portion on a wafer or in an in-die inspection area. Since regions with a high contrast and regions with a low contrast are mixed, the inspection accuracy can be enhanced by setting a sensitivity threshold to each region.

To enhance the sensitivity of an inspection apparatus, needs are increasing for segmentizing an in-die inspection area and setting a different sensitivity threshold to each segmentized area. In a known technique (e.g., PLT 1), by displaying a panoramic die image (a displayed image produced by synthesizing a plurality of sections selected from an acquired image) on the background of an in-die inspection area setting screen, an in-die inspection area can be set based on the image.

Other known techniques include a method of dividing an area based on a SEM image for application in inspection and an inspection method by means of matching between an SEM or optical image and a template image.

CITATION LIST

Patent Literature

PTL 1: JP 2010-283088 A

SUMMARY OF INVENTION

Technical Problem

However, in the technique of PTL 1, setting thousands or tens of thousands of in-die inspection areas requires repetition of an identical operation an excessive number of times.

Manually setting an in-die inspection area significantly lowers the efficiency and tends to cause human errors. However, human assistance is necessary to set different sensitivity thresholds to many in-die inspection areas, while maintaining the accuracy.

In the conventional technique, a large amount of time and labor is required for segmentation of regions for sensitivity enhancement, and inspection efficiency enhancement is difficult.

An object of the present invention is to provide a wafer appearance inspection apparatus that can segmentize an inspection target region, enable expedited execution of an operation to set a sensitivity threshold to each region, and enhance the inspection efficiency.

Solution to Problem

To achieve the foregoing objective, the present invention has the following features:

Light is irradiated to a wafer, and light having detected reflected light is displayed as an image in an image display portion. A part of an image distortion editing wafer, for which image processing is executed by an image processor, is defined as a template image. This template image is used to conduct pattern match processing with the entire image of the image distortion editing wafer in order to compute the pixel deviation of the image of the image distortion editing wafer. The computed pixel deviation is used to edit an image of an inspection target wafer, and an image region indicated by an operation portion is determined. An image region of which surface profile pattern is similar to the surface profile pattern of the determined image region is searched from among the other edited image regions of the inspection target wafer, and the searched image region is displayed on the image display portion. A sensitivity threshold for an image region indicated by the operation portion is set to the displayed image region. Based on the set sensitivity threshold, appearance inspection is conducted for the wafer.

From among the image data stored in a memory, data other than the data on image display region indicated by the operation portion is deleted. The data on the image display region indicated by the operation portion is read out and displayed on the image display portion. A sensitivity threshold setting image region indicated by the operation portion is determined. An image region of which surface profile pattern is similar to the surface profile pattern of the determined sensitivity threshold setting image region is searched from among the image regions displayed on the image display portion, and the searched image region is displayed on the image display portion. A sensitivity threshold for a sensitivity threshold setting image region by the operation portion is set. Appearance inspection is conducted for the wafer based on the set sensitivity threshold.

A sensitivity threshold setting image region indicated by the operation portion is determined. This sensitivity threshold setting image region is defined as a template image. This template image is used to conduct pattern matching with an image region of an inspection target wafer to acquire a matching candidate image. Based on the acquired image, the sensitivity threshold of the sensitivity threshold setting image region is set. Appearance inspection is conducted for the wafer based on the set sensitivity threshold.

Advantageous Effects of Invention

According to the present invention, there is provided a wafer appearance inspection apparatus that can segmentize an inspection target region, enable expedited execution of an operation to set a sensitivity threshold to each region, and enhance the inspection efficiency.

BRIEF DESCRIPTION OF DRAWINGS

FIGS. 6A to 6C are diagrams illustrating an operation for selecting and unselecting the searched in-die inspection area.

FIGS. 7A and 7B are diagrams illustrating a method of setting a search range for searching the similar in-die inspection area.

FIGS. 8A to 8C are diagrams illustrating a feature of automatically selecting an in-die inspection area along an image luminance edge when single in-die inspection area is selected.

FIGS. 9A and 9B are diagrams illustrating a feature of correcting the size of the single in-die inspection area so that the area is along the image luminance edge when the area, is selected.

FIGS. 10A to 10D are diagrams illustrating a feature of adjusting the set in-die inspection area along the image luminance edge.

FIGS. 11A and 11B are diagrams illustrating a feature of adjusting the scale of an image to be displayed according to a next operation content.

FIG. 12 is a diagram illustrating a feature of assigning different display colors to the set in-die inspection area based on set sensitivity threshold information.

FIG. 13 is a diagram illustrating a feature of estimating sensitivity threshold information based on image information on the set in-die inspection area.

DESCRIPTION OF EMBODIMENTS

The present invention is hereinafter described in reference to the attached drawings.

First Embodiment

Figure 1:
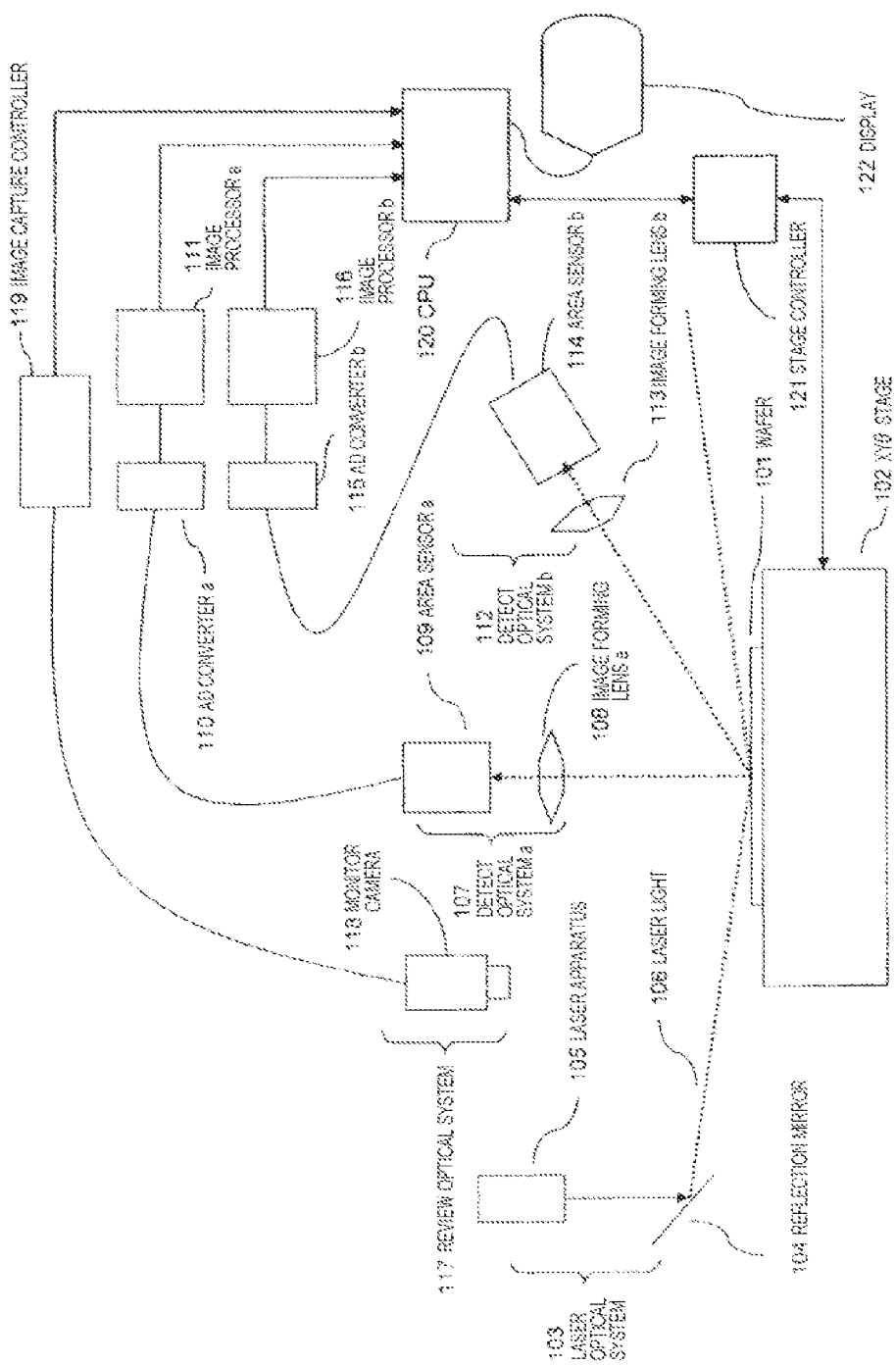
FIG. 1 is a diagram illustrating an example configuration of a wafer appearance inspection apparatus according to an embodiment of the present invention.

FIG. 1 is an overall general configuration diagram of a wafer appearance inspection apparatus according to one embodiment of the present invention.

As illustrated in FIG. 1, a laser optical system 103 has a laser apparatus 105 and a reflection mirror 104. Laser light 106 is irradiated from the laser apparatus 105 via the reflection mirror 104 to a wafer 101. An XYθ stage 102 is operated by a stage controller 121 to inspect the entire surface of the wafer 101.

Presence of an indentation or foreign substance on the surface of the wafer 101 causes the laser light 106 to scatter. The scattered light is detected by detect optical systems 107, 112. The detect optical system 107 has an image forming lens 108 and an area sensor 109. The detect optical system 112 has an image forming lens 113 and an area sensor 114.

The scattered light is converted by the detect optical systems 107, 112 into an electrical signal. The electrical signal is transmitted as image data via AD converters 110, 115 and image processors 111, 116 to a CPU 120, which is an operation controller.

In addition to the detect optical systems 107, 112, a review optical system 117 is disposed for inspection recipe preparation and defect inspection evaluation (detected defect review). A screen image acquired by a monitor camera 118 is processed by an image capture controller 119 and the CPU 120 and displayed on a monitor display 122.

Figure 15:
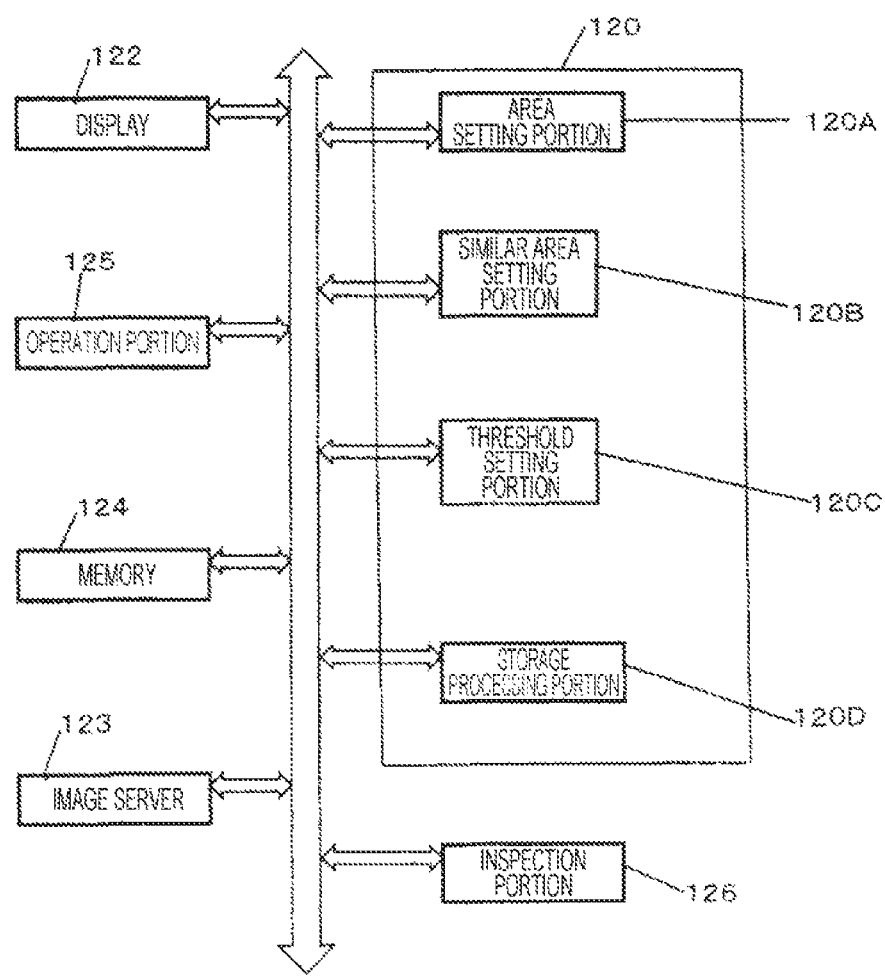
FIG. 15 is a block diagram of internal features of a CPU 120.

FIG. 15 is a block diagram of internal features of the CPU 120. As illustrated in FIG. 15, the CPU 120 includes an area setting portion 120A, a similar area setting portion 120B, a threshold setting portion 120C, and a storage processor 120D. The CPU 120 is connected to: an operation portion 125; a memory 124 that stores image data for which image processing has been performed and setting data; an image server 123; and an inspection portion 126 that inspects the appearance of an inspection target wafer. These connections of the CPU 120 are not illustrated in FIG. 1.

Figure 2:
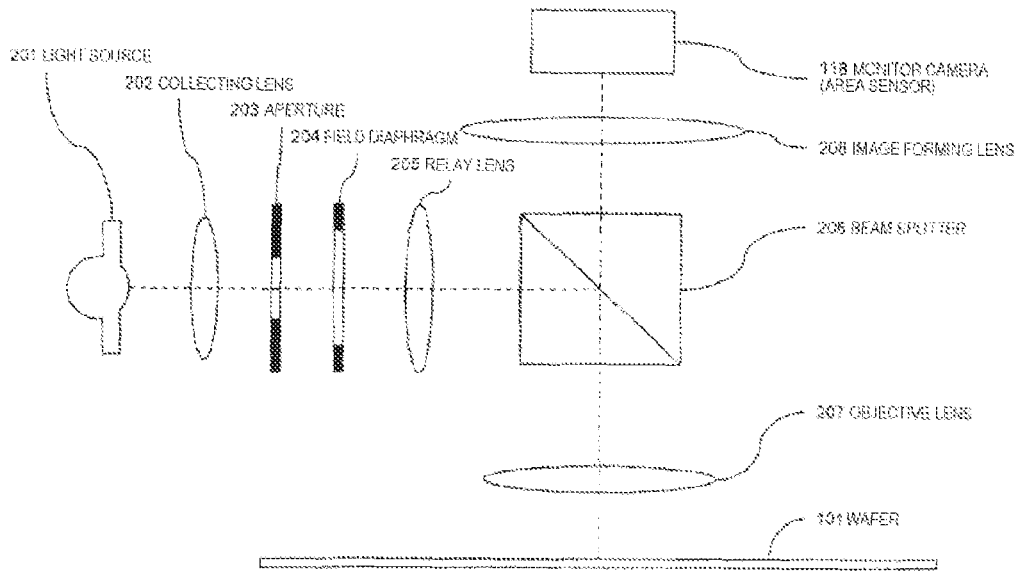
FIG. 2 is a diagram illustrating an example configuration of a review optical system of the wafer appearance inspection apparatus.

FIG. 2 is a diagram illustrating an example general configuration of the review optical system 117 in the wafer appearance inspection apparatus. As illustrated in FIG. 2, light emitted from a light source 201 is collected by a collecting lens 202. The brightness of the light collected by the collecting lens 202 is controlled by an aperture 203, and the review range of the aforementioned light is adjusted by a field diaphragm 204.

Thereafter, the light is reflected by a beam splitter 206 via a relay lens 205 and irradiated to the wafer 101 via the objective lens 207. The light reflected by the wafer 101 is, via the objective lens 207, transmitted through the beam splitter 206. Finally, the light travels through the image forming lens 208 and is converted into an electric signal by the monitor camera (area sensor) 118.

Figure 3:
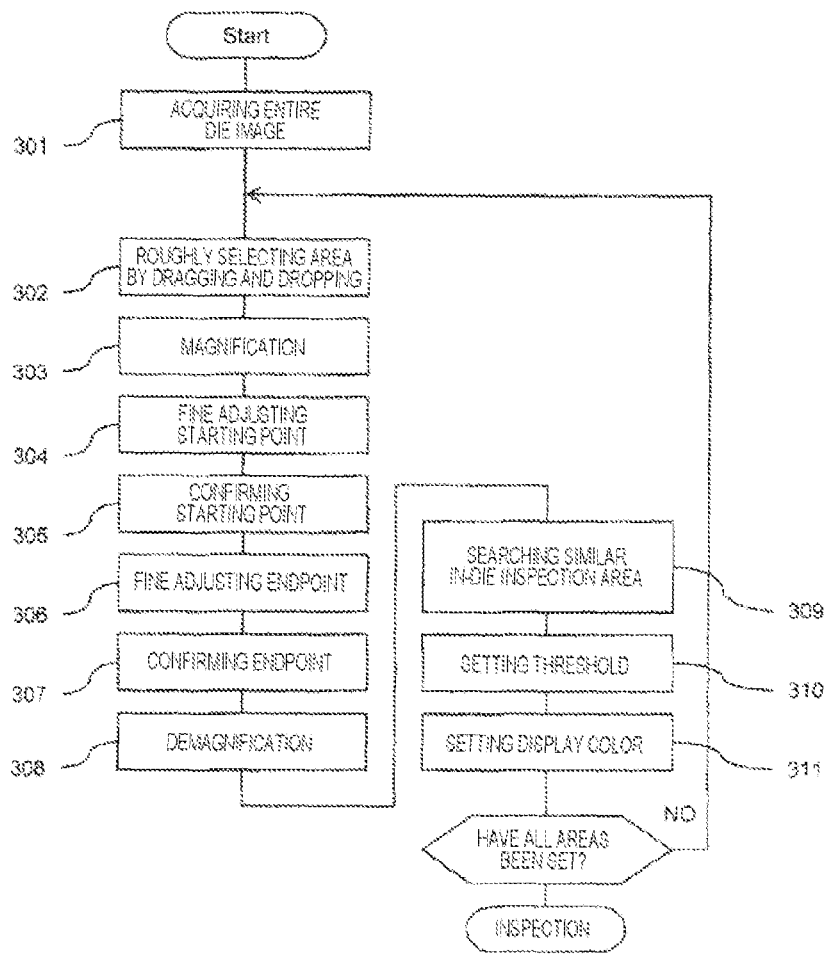
FIG. 3 is a diagram illustrating an example processing flow of a sensitivity-specified in-die inspection area setting process performed by the wafer appearance inspection apparatus.

FIG. 3 is a diagram illustrating an example processing flow or a sensitivity-specified in-die inspection area setting process performed by the wafer appearance inspection apparatus.

The processing of step 301 for acquiring an image of the entire die is described in reference to FIG. 1.

The wafer 101 is loaded on the XYθ stage 102. Alignment processing is performed to correct the slope of the wafer 101 on the XYθ stage 102. While the XYθ stage 102 is moved stepwise in the X and Y directions, the monitor camera 118 is used to successively acquire images of the wafer 101 and to store the acquired images in the image server 123. The foregoing operations are all automatically controlled by the CPU 120.

Since subsequent operations are performed using the acquired images stored in the server 123, these operations can be performed on another PC that can access the server 123.

Figure 4A:
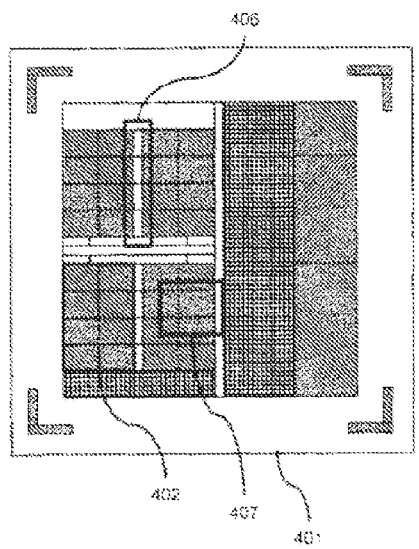
FIGS. 4A and 4B are diagrams illustrating an example display of a set in-die inspection area during the sensitivity-specified in-die inspection area setting process.
Figure 4B:
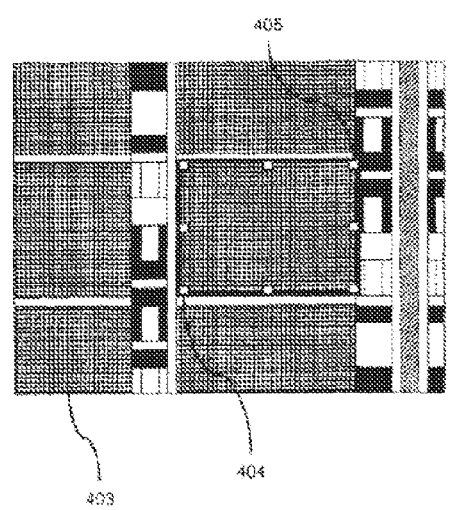

FIGS. 4(A) and 4(B) are diagrams illustrating example display of a set in-die inspection area during a sensitivity-specified in-die inspection area setting process. The foregoing is used to describe step 302, which is an area selection step of FIG. 3. In FIG. 4(A), a reference sign 401 denotes a schematic diagram of a panoramic synthesized image of the entire die, which is largely divided into two main portions: a cell area portion 402 and a logical portion 406.

The panoramic synthesized image 401 of the entire die is displayed on a PC or display 122 connected to the image server 123. On the panoramic synthesized image 401, an in-die area 407 is roughly selected by dragging and dropping (step 302 in FIG. 3).

In reference to FIG. 4, area magnification step 303 and fine adjustment step 304 to endpoint confirmation step 307 of FIG. 3 are described.

When the in-die area 407 is magnified on the display 122, the in-die area 407 is magnified as a magnified area 403 and displayed as illustrated in FIG. 4(B) (step 303 of FIG. 3). By dragging and dropping a starting point handle 404 and an endpoint handle 405, fine adjustment is performed for an area to be selected (steps 304 to 307 in FIG. 3).

FIGS. 8, 9 and 10 are diagrams illustrating a feature of automatically supporting fine adjustment of the starting point handle 404 and the endpoint handle 405 of FIG. 4 (corresponding to steps 304 to 307 of FIG. 3).

FIGS. 8(A) to 8(C) are diagrams illustrating a feature of automatically selecting an area along an image luminance edge by double-clicking when a single in-die inspection area is selected. FIGS. 9(A) and 9(B) are diagrams illustrating a feature of automatically selecting an area along an image luminance edge by dragging and dropping.

As illustrated in FIG. 8(A), to make a selection by means of double-clicking, double-clicking is performed within the boundary of an area 801 to be selected. As illustrated in FIG. 8(B), an image 802, of which edge is extracted by an image processing system of the CPU 120, is generated. A search is performed in four directions—i.e., in the upward, downward, left, and right directions—with reference to the clicked point so as to detect the first edge to be reached. A rectangular area 803 along edges (black frame) can be thereby selected, as illustrated in FIG. 8(C).

As illustrated in FIG. 9, to make a selection by means of dragging and dropping, the mouse pointer is brought to a candidate corner 901, which is the nearest to the mouse pointer, in order to highlight the candidate corner 901 (FIG. 9(A)). As illustrated in FIG. 9(B), when dragging and dropping is performed, an area surrounded by edges between proximate corners belonging to the starting point and endpoint of dragging is set as a selected area 903 (highlighted selection with a correction). A reference sign 902 denotes a highlighted selection without a correction.

FIGS. 10(A) to 10(D) are diagrams illustrating a feature of adjusting the selected area so as to be along an image luminance edge. In reference to FIGS. 10(A) to 10(D), a method of reducing the burden of fine adjustment of the selected area (steps 304 to 307 of FIG. 3) is described.

As illustrated in FIG. 10(A), when an arbitrary region 1002 is selected, an edge fit button 1001 displayed on the screen is pressed. As illustrated in FIG. 10(B), an image 802, of which edge is extracted by the image processing system of the CPU 120, is generated, and an edge 1003, which is near the four sizes of the region 1002, is detected. Each detected edge is modified, so as to be a rectangular (FIG. 10(C)) and a newly selected area 1004 (FIG. 10(D)).

FIGS. 11(A) and 11(B) is a diagram illustrating a feature of adjusting the scale of an image displayed according to operation content. A timing is determined for changing the scale of an image to be displayed as in the case of FIG. 3 where such a change is made in magnification display step 303 and demagnification step 308. According to the size of the region set in step 302(FIG. 11(A)), the magnified area 403 (FIG. 11(B)) is automatically displayed. Upon completion of the processing of endpoint confirmation step 307 of FIG. 3, the original-scale image 401 is automatically restored (step 308).

The operations of steps 302 to 308 are executed by the area setting portion 120A according to an operational instruction from the operation portion 125 and a display content of the display 122.

FIGS. 5 and 7 are diagrams illustrating an operation for searching a similar in-die inspection area. FIGS. 6(A) to 6(C) are diagrams illustrating an operation for selecting and unselecting the searched in-die inspection area. In reference to FIGS. 5 to 7, step 309 of FIG. 3 is described.

Figure 5A:
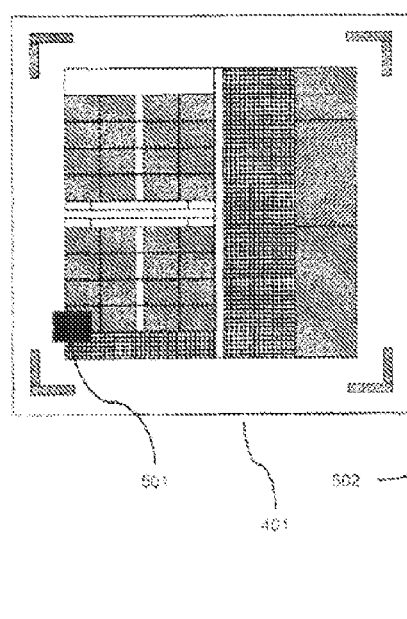
FIGS. 5A and 5B are diagrams illustrating an operation for searching a similar in-die inspection area.
Figure 5B:
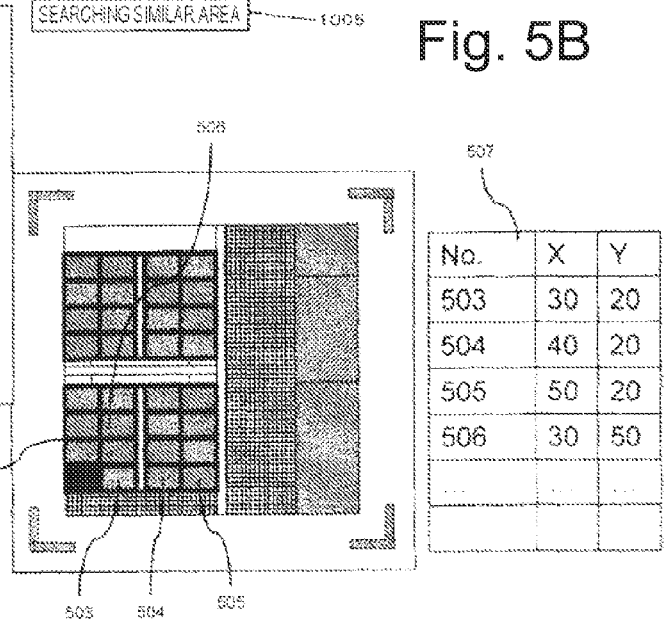

As illustrated in FIG. 5(A), a similar area search button 1005 is pressed when an in-die area 501 to be searched is selected. Pattern matching in which the search target area 501 is a template image is performed. As illustrated in FIG. 5(B), an area 502 with a similar surface profile pattern is highlighted as a similar area.

However, matching for the panoramic synthesized image 401 of the entire die, the area of which is very large, is a type of processing for which a large amount of time is expected to be taken. Thus, a method of performing a search in a limited area is used.

Figure 14:
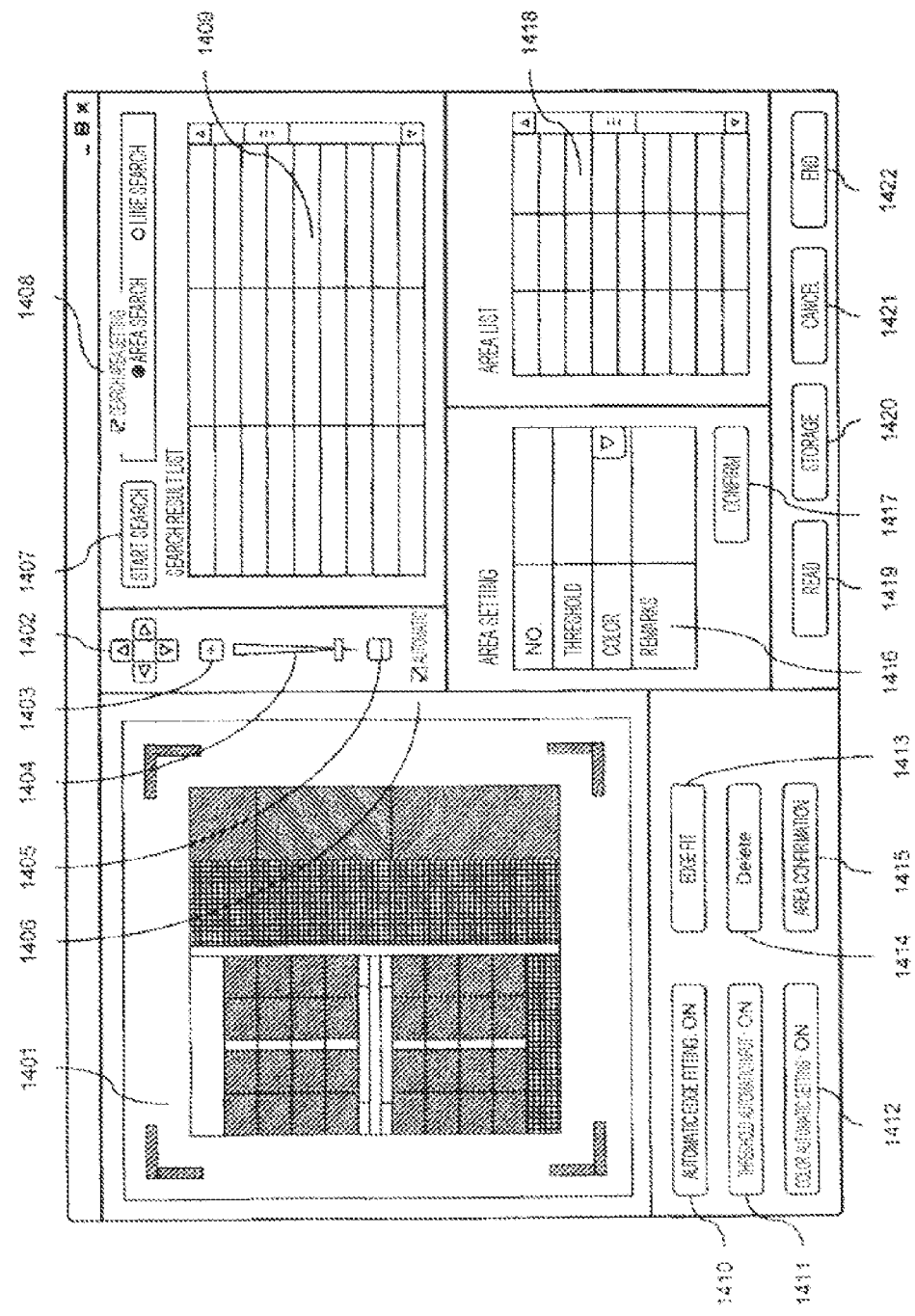
FIG. 14 is a diagram illustrating one example operation screen.

FIGS. 7(A) and 7(B) are diagrams illustrating a method of setting a search range in similar in-die inspection area search step 309. FIG. 14 is a diagram illustrating an example operation screen displayed on the display 122. In reference to FIGS. 7 and 14, the method of performing a search in a limited area is described.

Cell area portions tend to stick together in a certain range. Cell area portions, such as a region 702 as illustrated in FIG. 7(A), can be assumed as a search target area. In this assumption, a search area of the rectangular area defined by a dashed line 701 is set by means of dragging and dropping after pressing a search range setting (area search) button 1408 illustrated in FIG. 14.

Subsequently, matching is performed by pressing the similar area search button 1005 as illustrated in FIGS. 5(A) and 5(B).

When the search target area is a logical portion as illustrated in FIG. 7(B), the following procedure is performed:

Logical portions tend to be aligned in a certain direction. Logical portions, such as regions 704 as illustrated in FIG. 7(B), can be assumed as a search target area. In this assumption, after a search range setting (line search) button 1408 is pressed, the direction, such as the vertical or horizontal direction, and the width of a search area, such as a width 703, are set by means of mouse-clicking.

Thereafter, a similar area search button 1005 is pressed to perform matching.

As a result of matching, as illustrated in FIG. 5(B), the similar area 502 is highlighted, and a similar area list 507 is simultaneously displayed. The similar area list 507 is a list illustrating area numbers and XY coordinate pair values of the numbers. The similar area list 507 displays search candidates (regions 503 to 506) in a descending order of the similarity level.

Thereafter, by dragging within the image again, another area can be selected in the similar area 502 (a similar area 601 in FIG. 6(A)). The selected similar area 601 is highlighted in a color different from the color in which the similar area 502 is highlighted. As illustrated in FIG. 6(B), the similar area list 507 is associated with the similar area

601, and the area selected in the similar area 601 is highlighted as in the case of a section 602.

Subsequently, by pressing a confirm button 1417, only the selected similar area is confirmed and remained as a selected area 603 (FIG. 6(C)). Conversely, by pressing a delete button 1414, only the selected search candidate 601 can be removed from among the search candidates.

Step 309 is performed by the similar area setting portion 120B.

FIG. 13 is a diagram illustrating a feature of estimating sensitivity threshold information based on image information on the set in-die inspection area, which is processing corresponding to the processing of step 310 of FIG. 3. One reason for segmentizing an area and assigning a threshold to each segmented area is that a high image contrast area that is in practice free from defect—e.g., a logical portion 1302—is more likely to be misjudged to be defective than a low contrast area—e.g., a cell area portion 1301.

This likelihood arises since when a difference between two images is identified upon detection of a defect, an error between pixels (quantification error) is more likely to be evident in a high contrast region.

A value corresponding to the image contrast within an area (e.g. σ value denoting the gray level of each pixel (image luminance deviation) is automatically set as an initial value. The value set as the initial value is displayed on the screen (a threshold display portion illustrated in FIG. 14), so that the value is changeable for an operator. If the sensitivity threshold should remain as the set initial value, no changing operation needs to be performed.

FIG. 12 is a diagram illustrating one example of assigning different display colors to the set in-die inspection area based on the set sensitivity threshold, which corresponds to the processing of step 311 of FIG. 3.

In the example illustrated in FIG. 12, seven colors ranging from red to purple (C1 to C7) are set so that the thresholds of C1 to C7 are in an ascending order. Display colors are set to distinguish the sensitivity thresholds of the set area. By automatically displaying a color of which hue corresponds to the threshold, a mistake in inputting a setting value and data omission can be made evident by color.

The processing of steps 310 and 311 is executed by the threshold setting portion 120C.

By the foregoing processing, setting of one group is completed. If there is another region to be set, the process needs to be returned to step 302 so that steps 302 to 311 are performed.

Upon completion of setting of the entire in-die inspection area, the setting is stored in the memory 124 by the storage processor 120D, and an area setting file is transferred to the inspection portion 126. The inspection portion 126 uses the area setting file thus transferred in order to inspect an inspection target. The foregoing is a flow of inspection.

FIG. 14 is a diagram illustrating one example of an operation screen displayed on the display 122. As illustrated in FIG. 14, an automatic edge fit button 1410, a threshold automatic input button 1411, a color automatic setting button 1412, an edge fit button 1413, a delete button 1414, and an area setting button 1415 are displayed under a panoramic image display region 1401.

Other buttons include a horizontal and vertical movement button 1402, magnification and demagnification buttons 1403 to 1405, an automatic button 1406, a search start button 1407, a search area setting button 1408, a search result display region 1409, an area setting region 1416, a confirm button 1417, an area list region 1418, a read button 1419, a storage button 1420, a cancel button 1421, and an end button 1422.

The operation screen of FIG. 14 is used to execute a task of segmentizing an inspection target region for each set threshold.

As described in the foregoing, according to one embodiment of the present invention, there are provided: a wafer appearance inspection apparatus that can segmentize an inspection target region, enable expedited execution of an operation to set a sensitivity threshold for each region, and enhance the inspection efficiency; and a method of sensitivity threshold setting.

The operation of the wafer appearance inspection apparatus can be thereby partially automated and simplified to reduce the hours and burden of repetitive manual work.

Second Embodiment

Figure 22:
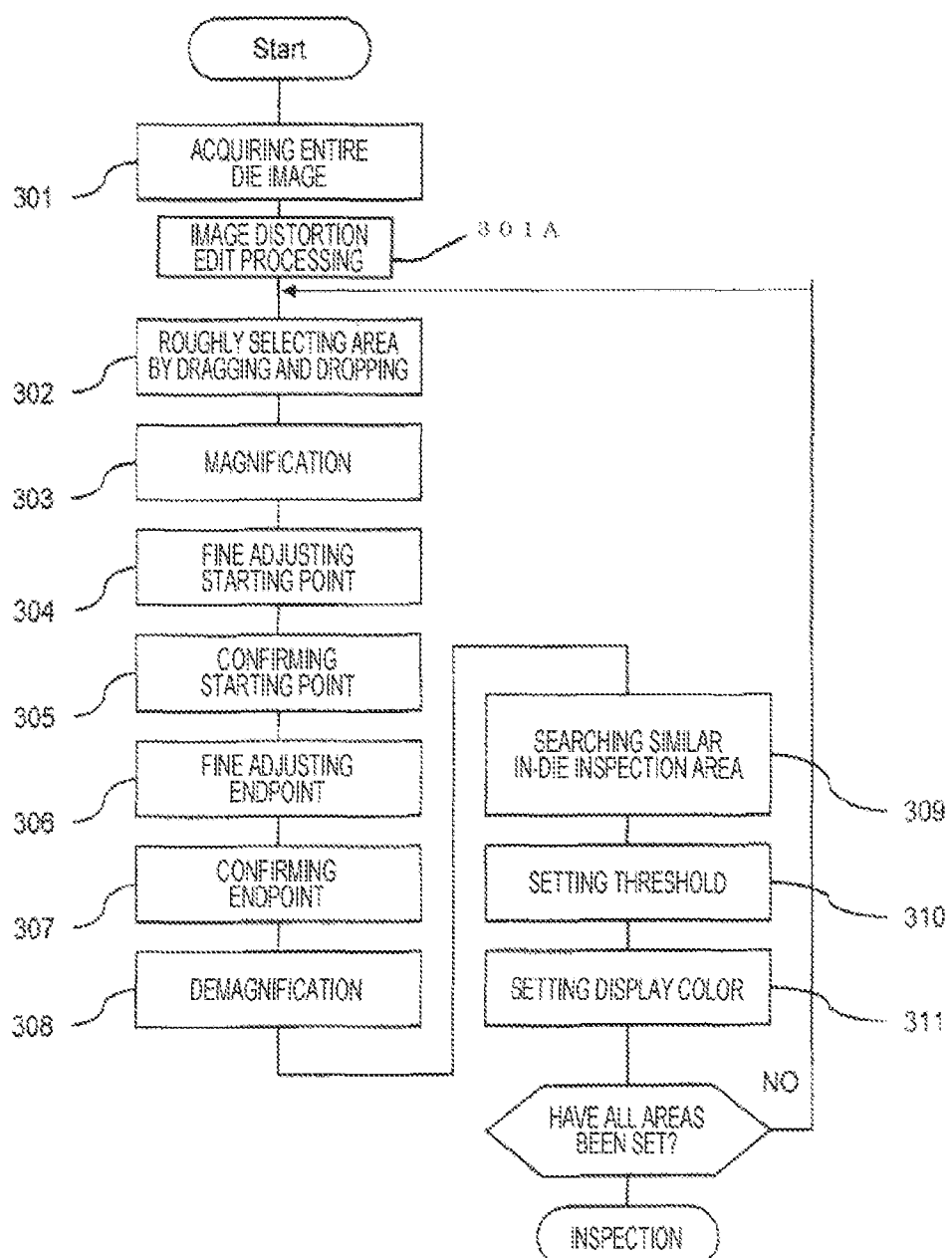
FIG. 22 is an operation flowchart O of the second embodiment of the present invention.

A method of editing the distortion of a component image acquired in step 301 of FIG. 3 is hereinafter described. An image distortion editing value is computed prior to step 301 of FIG. 3 of the first embodiment, and image distortion edit processing is performed for an image acquired in step 301. FIG. 22 is a flowchart of a second embodiment of the present invention, in which image distortion edit processing step 301A is added between steps 301 and 302 of FIG. 3. The other steps illustrated in FIG. 22 are identical to the steps illustrated in FIG. 3.

In FIG. 22, after an image of the entire die illustrated in step 301 is acquired, a synthesized image is displayed. However, when there is a distortion in a synthesized component image, misalignment occurs at the boundary with an adjacent synthesized component image. According to the present invention, an area is set in reference to an image displayed in the background, and a high coordinate accuracy is required for the displayed image.

When the cause of image distortion is traced to the apparatus, the image display accuracy needs to be secured by editing the distortion of an image to be shot in advance.

Figure 16:
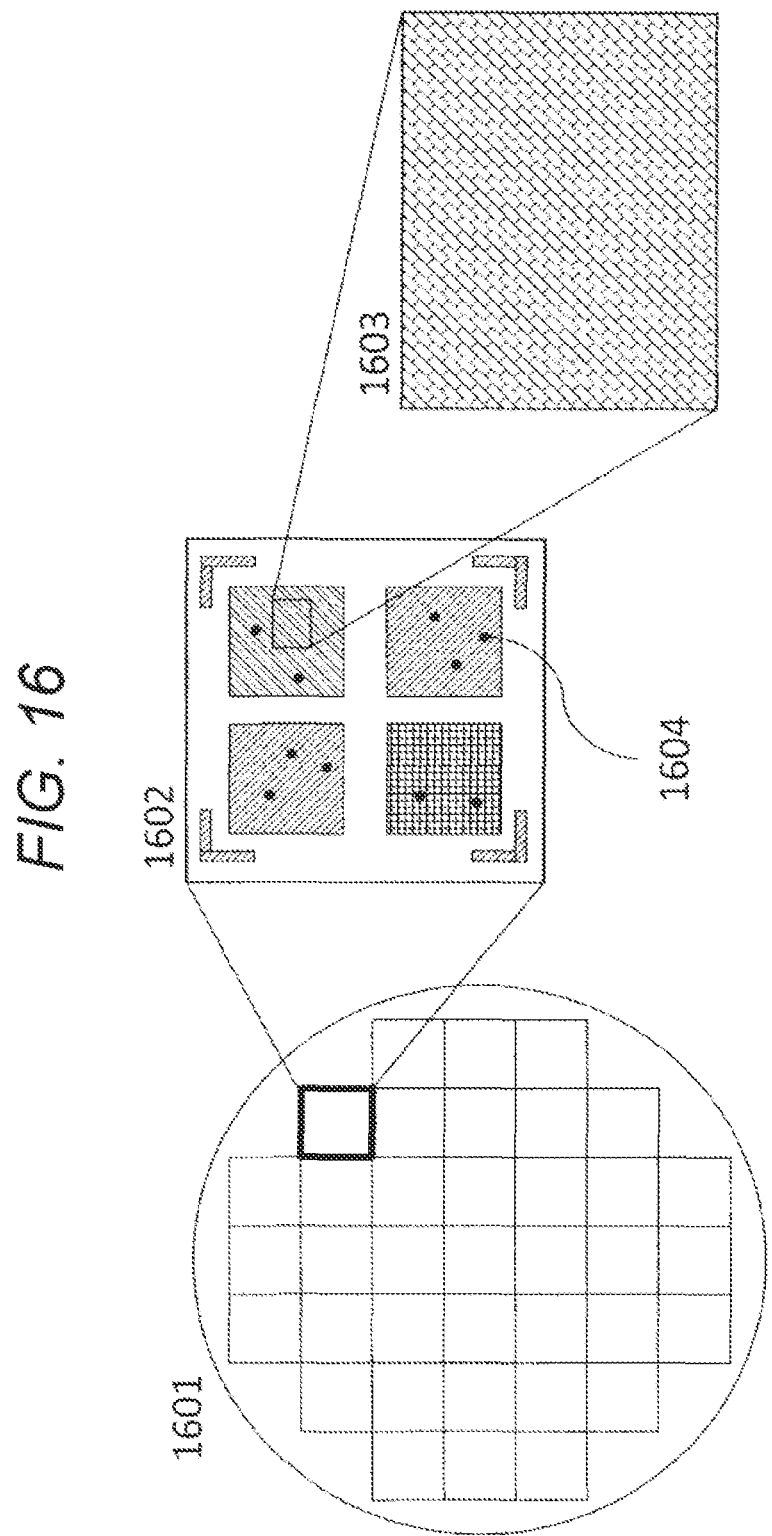
FIG. 16 is a diagram illustrating an example standard wafer.

FIG. 16 is a diagram illustrating an example standard wafer (image editing wafer) 1601 for sensitivity adjustment. According to this embodiment, the standard wafer 1601 is used to edit image distortion. A plurality of dies 1602 are arranged in the standard wafer 1601. Intentionally made defects 1604 are included inside the dies 1602, and the sensitivity of the inspection apparatus is determined by confirming whether the apparatus can find the defect. The foregoing image distortion edit processing is executed by the area setting portion 120A.

Figure 17:
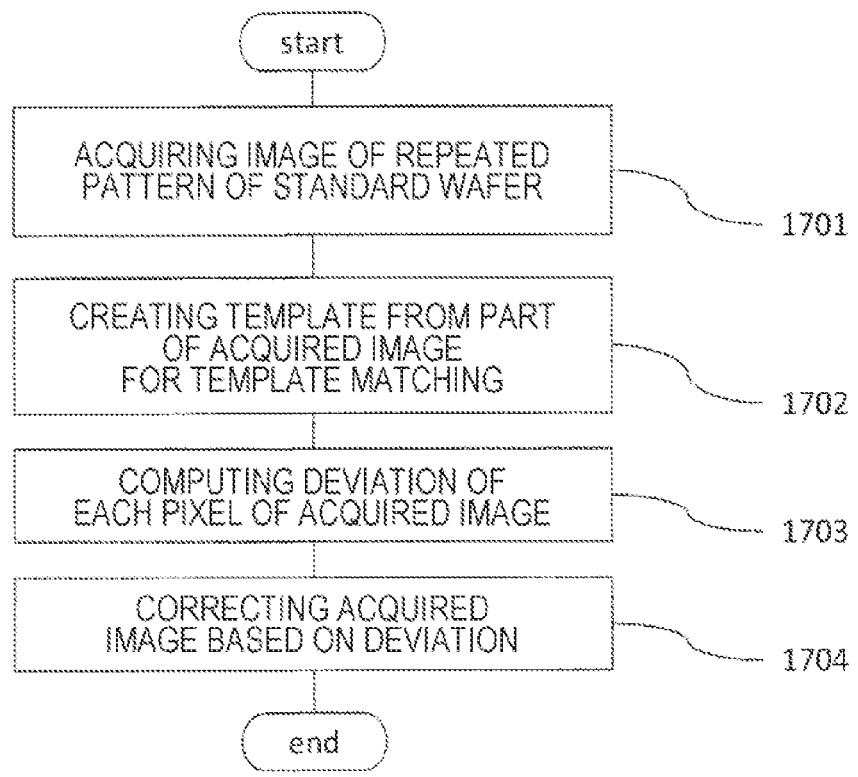
FIG. 17 is a diagram illustrating a processing flow of image distortion correction processing according to a second embodiment of the present invention.
Figure 18:
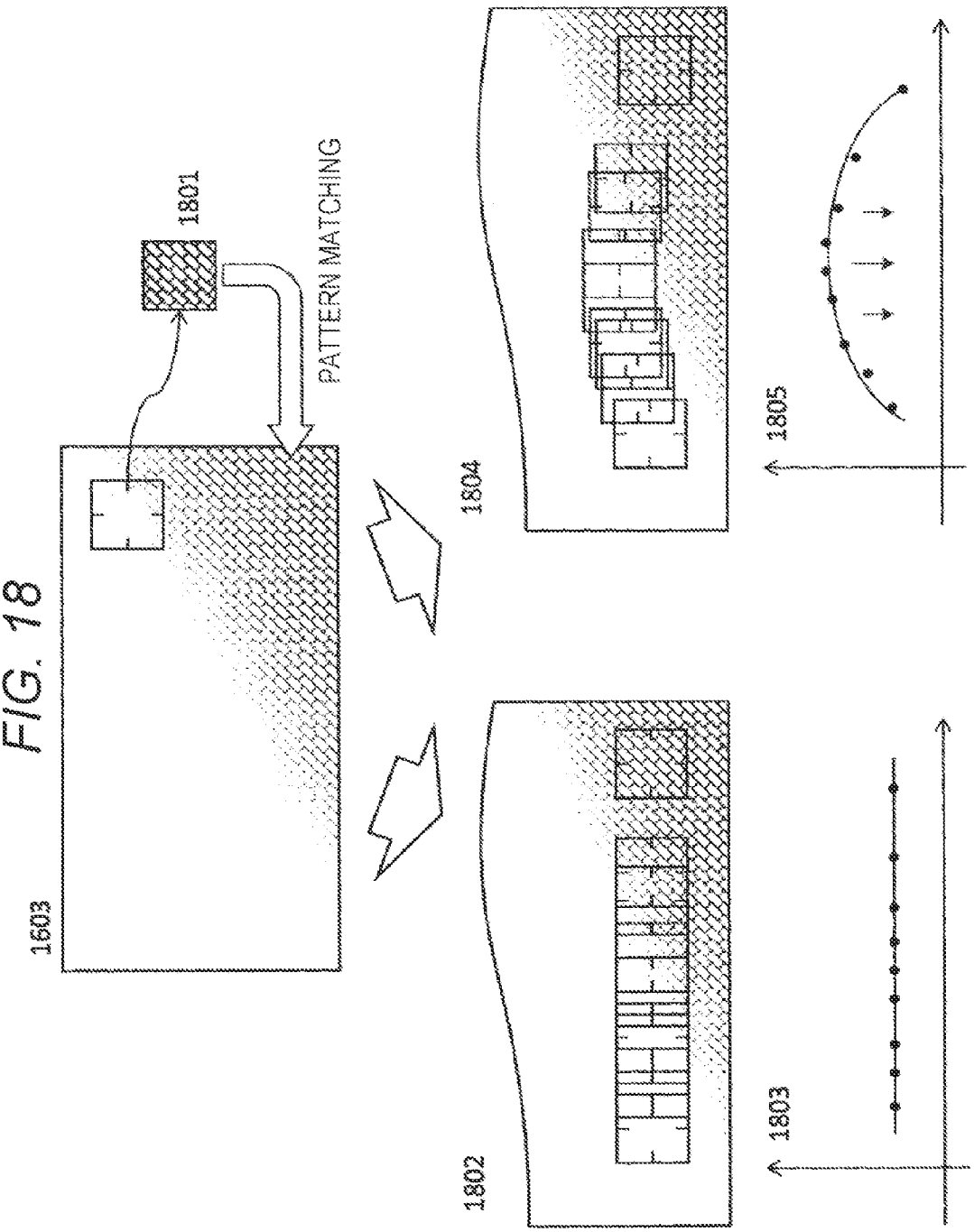
FIG. 18 is a diagram illustrating a summary of image distortion correction processing according to the second embodiment of the present invention.

FIG. 17 is a diagram illustrating a specific processing flow of image distortion edit processing (image distortion correction processing). In reference to FIG. 18, each processing step of FIG. 17 is described. Each processing step of FIG. 17 is executed by the area setting portion 120A.

First of all, a part 1603, which is a part of the die 1602 of the standard wafer 1601 and in which an identical pattern is repeated, is acquired (step 1701). It is desirable that the identical repeated pattern is shown in the entire image of the acquired part 1603. A part of the acquired image is defined as a template image 1801, and template matching is performed for the entire image of the part 1603 (step 1702).

In turn, processing step 1703 is hereinafter described. As can be seen in image regions 1802, 1084, which illustrate a part of the template matching result in step 1702, matched coordinate pairs should be neatly aligned on a distortion-free image, such as the image region 1802. As illustrated in a graph 1803, matched images are arranged in a straight line.

To the contrary, when images are distorted, the images are bent or inclined as illustrated in an image region 1804. As illustrated in a graph 1805, matched images are arranged in a curved path.

By this method, it is possible to numericalize the amount of the deviation of a specific pixel within an image, compute a correction value for making a correction to toward the direction opposite to the deviation, and multiply image data (a component, image of a synthesis target) by the computed correction value in order to correct the distortion (steps 1703 and 1704).

FIG. 17 illustrates an operation flow of an image distortion correction processing (edit processing) in sequence. Steps 1701 to 1703 of FIG. 17 are executed prior to step 301 illustrated in FIG. 22. The processing of step 1704 is executed for an linage acquired in step 301. The processing content of step 1704 is identical to the processing content of step 301A.

It is desirable that the size of the template 1801 is sufficiently smaller than the size of the image 1603 (e.g., approximately ⅟₁₆ of the size of the entire image). Also, it is desirable that the size of a repeated pattern is sufficiently smaller than the size of the template 1801.

Here, a part of the standard wafer 1601 for sensitivity adjustment is used. A part where an identical pattern is repeated can be edited by any wafer.

As editing can be conducted by the existing wafer, no additional cost is needed for editing.

By editing an image in advance, the distortion caused by the difference in the type of camera or apparatus is reduced, and a smoothly synthesized image with a small amount deviation can be acquired.

This editing method is applicable for, inter alia: editing of the distortion specific to the inside of the camera; correction of the image distortion due to the gradient, rotation, and the like of a camera placed on a fixture; and measurement of camera image distortion changes over time.

Aforementioned fourth embodiment is used for editing image distortion during a sensitivity threshold setting operation for an inspection target region. However, the fourth embodiment can also be used for operations other than sensitivity threshold setting, such as an operation in which image distortion editing is necessary.

The processing subsequent to the synthesized image display step is not specifically described as the aforesaid processing is identical to the processing of the first embodiment.

Third Embodiment

A third embodiment of the present invention is hereinafter described. The third embodiment of the present invention is an example method of displaying many images so that the storage space of the memory 124 is saved and an area is set without causing an operational delay. This method is performed for displaying a synthesized image by the area setting portion 120A after step 301 of FIG. 3 of the first embodiment.

Figure 19:
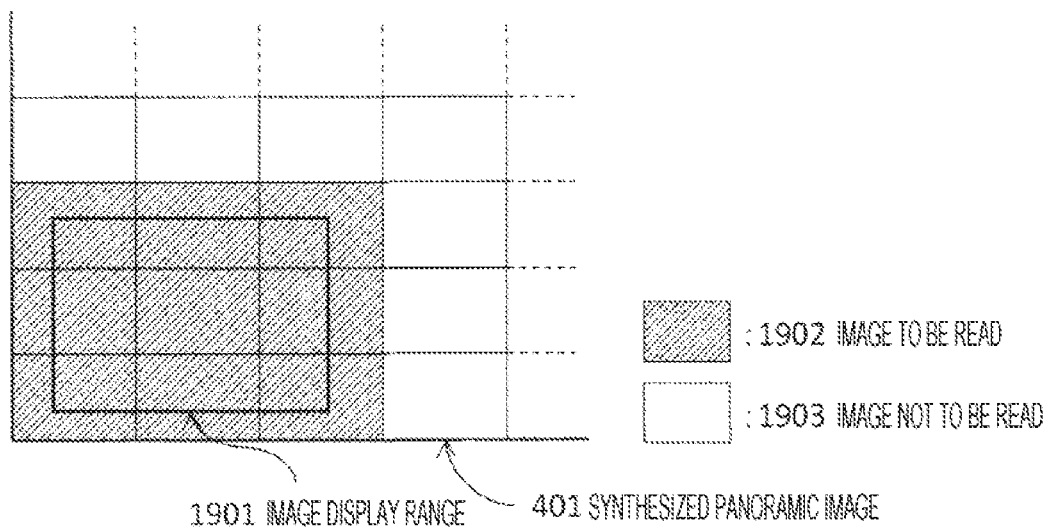
FIG. 19 is a diagram illustrating a relationship between a screen display range and an image to be read thereinto according to a third embodiment of the present invention.

FIG. 19 is a diagram illustrating the relationship between the screen display range and an image to be read thereinto. In reference thereto, the method of saving the storage space of the memory 124 is described.

When images acquired using a high-precision microscope are synthesized as one image without reduction, the size of the aforesaid one image amounts to tens of thousands of pixels×tens of thousands of pixels. The storage space of the memory 124 is used up by handling this image, and it is difficult to handle this image by an ordinary processing system. Accordingly, the memory storage space is saved by performing the following: retaining an image display range 1901; reading and displaying only the image 1902 drawn on (within the display range of) the display 122; and deleting, from the memory 124, an image 1903 not drawn thereon (not within the display range thereof).

As access to the image server 123 is necessary for image read processing and this processing is time-consuming, image read processing is parallelized. Display of a background image thereby needs to be performed subsequently, but an area setting operation can be performed real-time without stress.

Figure 20:
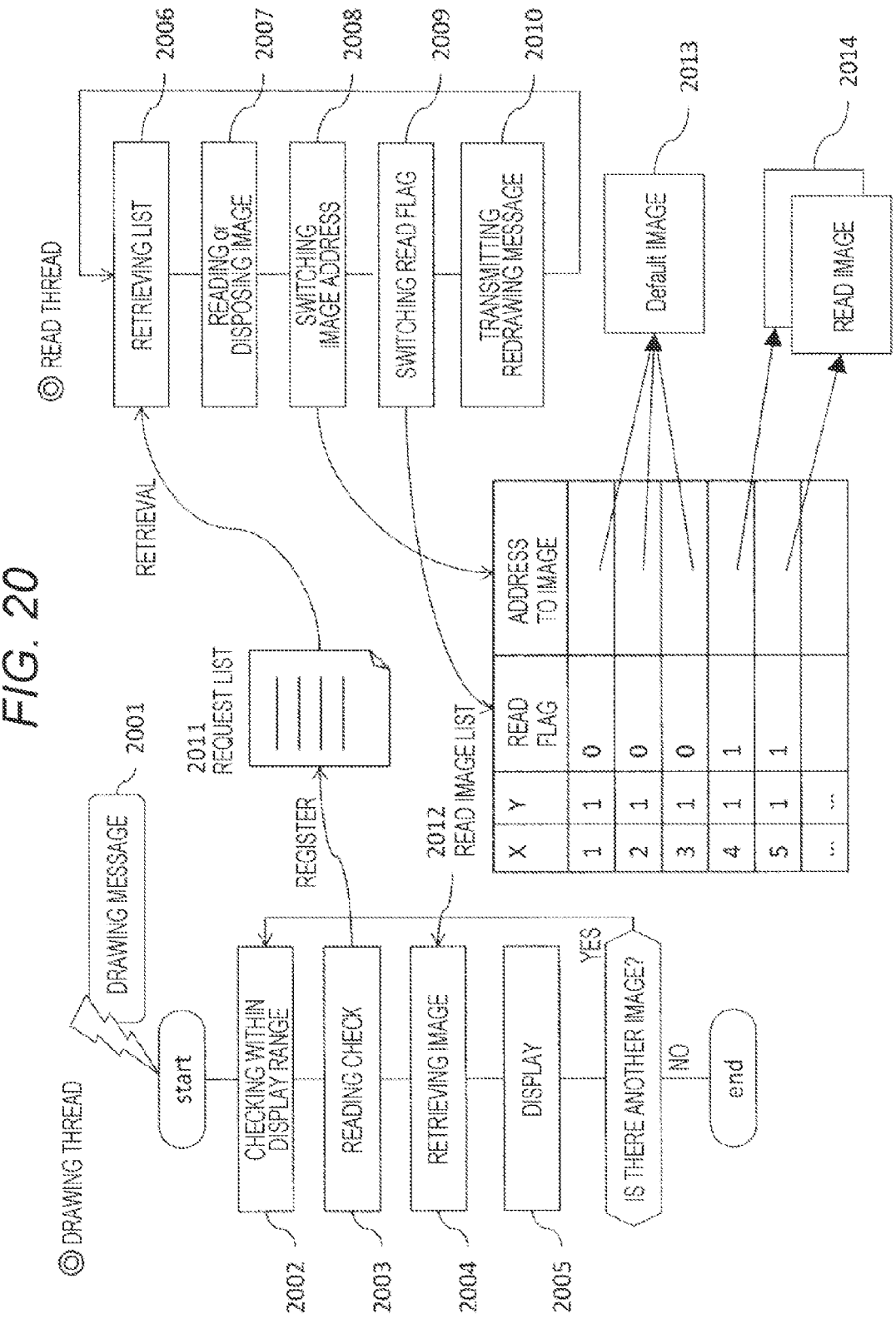
FIG. 20 is a diagram illustrating a processing flow of parallelized image read processing according to the third embodiment of the present invention.

FIG. 20 is a diagram illustrating a processing flow of parallelized image read processing. In reference thereto, the parallelized processing is described.

In FIG. 20, image processing is divided into a drawing thread of drawing on an image and a reading thread reading from a file.

First of all, the processing of the drawing thread is described.

In the processing for drawing on a part of the screen, a drawing message is passed from an OS (operating system) (step 2001), and drawing is executed in a message handler. After acquired component images are scanned in order, whether the image can be drawn on the screen is checked (step 2002), and whether reading has been completed is checked (step 2003).

If the image is to be drawn (within the display range) and has not been read yet, a read request is registered in a request list 2011. Addresses of image data stored in a read image list 2012 (in this case, default image (default image) 2013) are retrieved (step 2004) and drawn on the screen (step 2005).

If the image is to be drawn (within the display range) and has already been read, addresses of image data stored in a read image list 2012 (read image 2014) are retrieved and drawn on the screen.

If the image is not to be drawn (not within the display range) and has not been read yet, the processing proceeds to checking of a next image (return to step 2002).

If the image is not to be drawn (not within the display range) and has already been read, a disposal request (deletion request) is registered in the request list. After all images are scanned, the drawing thread has gone through the processing stage and has been completed.

In turn, the processing for the reading thread is described.

In processing step 2006, whether there is a request in the request list 2011 is checked, and the request is retrieved from the list if there is (step 2006). In step 2007, the content of the retrieved request is examined, and an image is read if the request is a read request. The situation where the request is not a read request, but a disposal request in step 2007 will be described below.

In steps 2008 and 2009, the read image list 2012 is scanned, and addresses of images in the relevant image rows are switched from the addresses of the default image 2013 to the addresses of the newly read image 2014. A read flag is shown in step 2009. Finally, in step 2010, a redraw message is transmitted to the OS. Upon transmission of this message, a draw message 2001 is issued from the OS at an appropriate timing, and the draw processing thread is launched.

The situation where the request retrieved in step 2007 is a disposal request is hereinafter described.

If the request is a disposal request, image information is disposed in step 2007, and the address of the image is switched to a default image in step 2008. Also, the read flag is cancelled in step 2009. In this case, a draw request message is not transmitted.

By parallelizing the processing as described above, an area setting operation can be performed real-time without stress even if image drawing is time-consuming. According to the third embodiment of the present invention, many images can be displayed so that the storage space of the memory 124 is saved, and an area can be set without causing an operational delay.

The processing subsequent to the synthesized image display step is not specifically described as the aforesaid processing is identical to the processing of the first embodiment.

Fourth Embodiment

A fourth embodiment of the present invention is hereinafter described. According to the fourth embodiment, match processing for searching a similar area in processing step 309 of FIG. 3 is performed as template match processing for a synthesized image 401 constituted by patching (synthesizing) a plurality of images.

Figure 21:
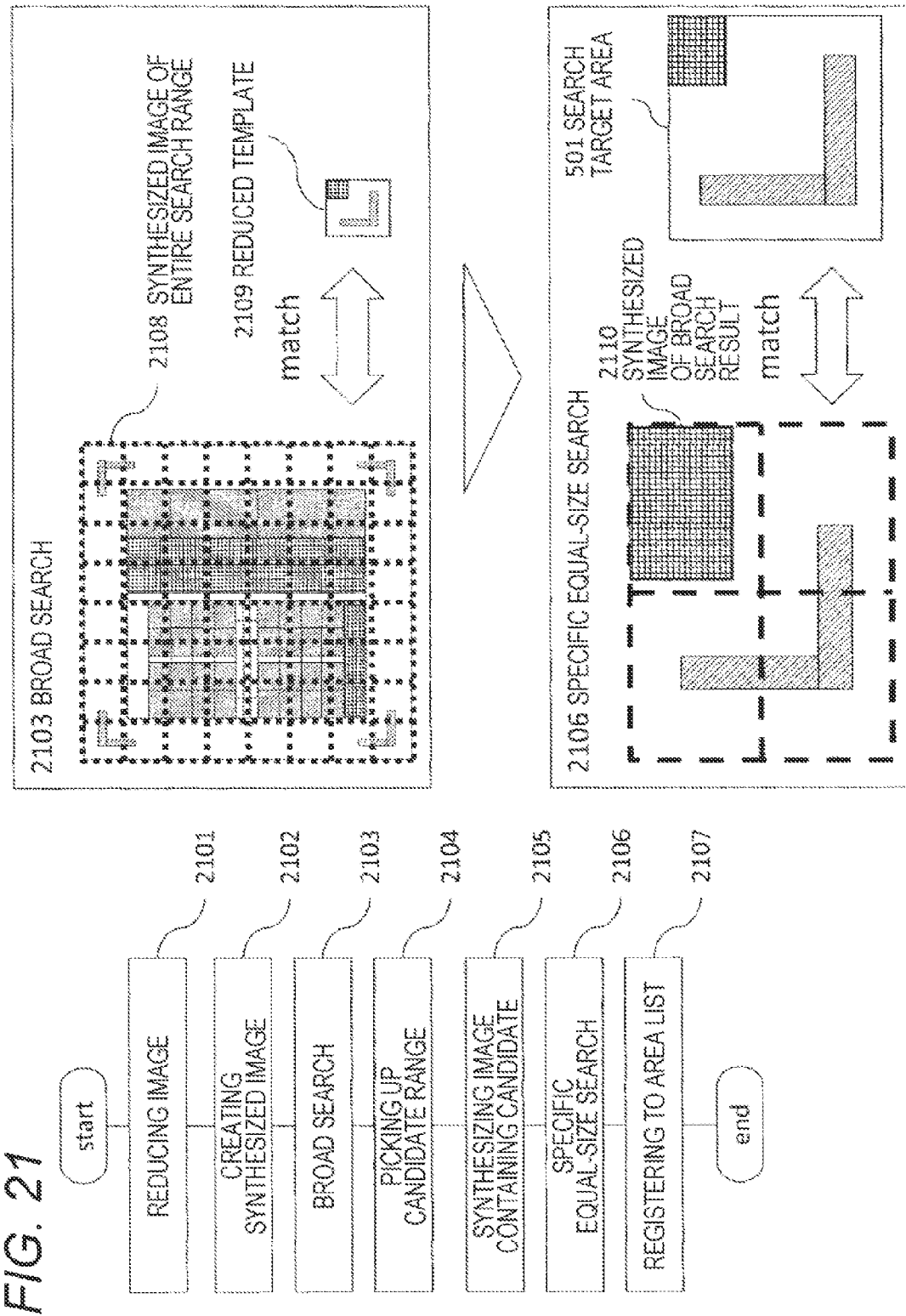
FIG. 21 is a diagram illustrating a processing flow and summary of match processing for a patched image according to the fourth embodiment of the present invention.

FIG. 21 is a diagram illustrating a processing flow and summary of match processing for a patched image (synthesized image) in the fourth embodiment of the present invention. In reference thereto, the fourth embodiment is hereinafter described.

An example illustrated in FIG. 21 is where search is performed in two main steps: broad search 2103 and specific search 2106.

In processing step 2101, all images within the matching target range are reduced. The reduction rate depends on the processing system, but the synthesized image size needs to be equal to or smaller than the size that can be handled by the processing system. For instance, reduction is made so that the synthesized image size is 4096×4096 or smaller.

In turn, the images reduced in processing step 2102 are synthesized to produce a synthesized image 2108 of the entire search range. The reduced search target area 501 is reduced to a reduction template 2109 so that template matching with the entire synthesized image 2108 is performed. Such is defined as broad search (step 2103).

The coordinate pair of a matching candidate derived from the broad search result is picked up in processing step 2104. Subsequently, in step 2105, based on the coordinate pair of the matching candidate, an equal-size synthesized image 2110 containing the matching candidate range is produced.

Using the search target area 501 as a template, template matching is performed for the synthesized image 2110 derived from the broad search result. Such is called specific equal-size search (step 2106).

Finally, in processing step 2107, the coordinate pair of the matching candidate confirmed by the specific search is registered in the similar area list 507.

If a plurality of matching candidates is found by the broad search in step 2103, specific search (step 2106) is performed as many times as the number of the matching candidates.

When a search area (701, 703) is set prior to the aforementioned processing, the reduction ratio is small in step 2101, and the processing speed and accuracy of the broad search (step 2103) increase.

The operation subsequent to the synthesized image matching step is not specifically described as the aforesaid operation is identical to the operation of the first embodiment.

The fourth embodiment of the present invention enables expedited execution of template matching for a synthesized image r and an operation for setting a sensitivity threshold for each region.

REFERENCE SIGNS LIST

101 wafer
102 XYθ stage
103 laser optical system
104 reflection mirror
105 laser apparatus
106 laser light
107 detect optical system a
108 image forming lens a
109 area sensor a
110 AD converter a
111 image processor a
112 detect optical system b
113 image forming lens b
114 area sensor b
115 AD converter b
116 image processor b
117 review optical system
118 monitor camera
119 image capture controller
120 CPU
121 stage controller
122 display
123 image server
124 memory
125 operation portion
126 inspection portion
201 light source
202 collecting lens
203 aperture
204 field diaphragm
205 relay lens
206 beam splitter
207 objective lens
208 image forming lens
401 panoramic synthesized image
402 cell area portion
403 magnified image
404 starting point handler
405 endpoint handler
406 logical portion
407 in-die area
501 search target area
502 highlighted similar area
503 similar area 1
504 similar area 2
505 similar area 3
506 similar area 4
507 similar area list
601 selected and highlighted similar area
602 area corresponding to 601 in list
603 selected area highlighted after confirmation
701 search area (area selection type)
702 selected and highlighted cell area portion
703 search area (line selection type)
704 selected and highlighted logical portion
801 region to be selected 802 edge extraction image
803 selected region
901 selected and highlighted candidate corner
902 selected and highlighted without correction
903 selected and highlighted with correction
1001 edge fit button
1002 selected and highlighted prior to processing
1003 extracted edge
1004 selected and highlighted subsequent to processing
1301 cell area portion
1302 logical portion
1601 standard wafer
1602 die
1601 repeated pattern image extracted from part of die
1604 intentionally made defect
1801 template image
1802 matching result (without distortion)
1803 graph illustrating coordinate pair value of matching result (without distortion)
1804 matching result (with distortion)
1805 graph illustrating coordinate pair value of matching result (with distortion)

The invention claimed is:

1. A wafer appearance inspection apparatus comprising:
a light source that irradiates light to an inspection target wafer;
a light detector that detects light reflected from the inspection target wafer;
an image processor that converts, into an image, the light detected by the light detector;
an image display portion;
an operation portion that inputs an operational instruction; and
an operation control portion that performs:
defining, as a template image, a part of an image distortion editing wafer for which image processing is performed by the image processor;
pattern match processing with an entire image of the image editing wafer using the template image;
computing a pixel deviation of the image of the image editing wafer;
editing the image of the inspection target wafer using the computed pixel deviation;
determining an image region indicated by the operation portion;
searching an image region, a surface profile pattern of which is similar to a surface profile pattern of the determined image region, from among other image regions of the edited inspection target wafer, and displaying the searched image region on the image display portion; and
setting a sensitivity threshold for the image region indicated by the operation portion,
such that an appearance of the wafer is inspected based on the sensitivity threshold set by the operation control portion.

2. A wafer appearance inspection apparatus comprising:
a light source that irradiates light to an inspection target wafer;
a light detector that detects light reflected from the inspection target wafer;
an image processor that converts, into an image, the light detected by the light detector;
a memory that stores image data for which image conversion is performed by the image processor;
an image display portion;
an operation portion that inputs an operational instruction; and
an operation control portion that performs:
obtaining, from the operation portion, an image display region on the image display portion;
deleting, from among image data stored in the memory, image data that are not within the image display region indicated by the operation portion;
reading out image display region data indicated by the operation portion and displaying only the image display region data that are within the image display region on the image display portion;
determining a sensitivity threshold setting image region indicated by the operation portion;
searching, from among image regions displayed on the image display portion, an image region of which surface profile pattern is similar to a surface profile pattern of the determined sensitivity threshold setting image region, and displaying the searched image region on the image display portion; and
setting a sensitivity threshold to the sensitivity threshold setting image region indicated by the operation portion,
such that an appearance of the wafer is inspected based on the sensitivity threshold set by the operation control portion.

3. A wafer appearance inspection apparatus comprising:
a light source that irradiates light to an inspection target wafer;
a light detector that detects light reflected from the inspection target wafer;
an image processor that converts, into an image, the light detected by the light detector;
an image display portion;
an operation portion that inputs an operational instruction; and
an operation control portion that performs:
determining a sensitivity threshold setting image region indicated by the operation portion;
reducing the sensitivity threshold setting image region and an image region of the inspection target wafer;
defining the reduced sensitivity threshold setting image region as a template image;
pattern matching with the reduced image region of the inspection target wafer;
acquiring an matching candidate image; and
based on the acquired image, setting a sensitivity threshold to the sensitivity threshold setting image region,
such that an appearance of the wafer is inspected based on the sensitivity threshold set by the operation control portion.

4. A wafer appearance inspection apparatus comprising:
a light source that irradiates light to an inspection target wafer;
a light detector that detects light reflected from the inspection target wafer;
an image processor that converts, into an image, the light detected by the light detector;
an image display portion;
an operation portion that inputs an operational instruction; and
an operation control portion that performs:
determining a sensitivity threshold setting image region indicated by the operation portion;
defining the sensitivity threshold setting image region as a template image;

pattern matching with an image region of the inspection target wafer;
acquiring an matching candidate image; and
based on the acquired image, setting a sensitivity threshold to the sensitivity threshold setting image region, such that an appearance of the wafer is inspected based on the sensitivity threshold set by the operation control portion, wherein the operation control portion performs:
reducing the sensitivity threshold setting image region and the image region of the inspection target wafer;
defining the reduced sensitivity threshold setting image region as a template image;
pattern matching with the reduced image region of the inspection target wafer;
acquiring a matching candidate image;
restoring an image from the acquired matching candidate image so that a size of the restored image is equal to a pre-reduction size;
pattern matching with a pre-reduction image region of the inspection target wafer;
acquiring a matching candidate image; and
based on the acquired image, setting a sensitivity threshold to the sensitivity threshold setting image region.

* * * * *